(12) United States Patent
Kim et al.

(10) Patent No.: US 8,003,348 B2
(45) Date of Patent: Aug. 23, 2011

(54) METHOD FOR THE MASS EXPRESSION OF AN ANTIMICROBIAL PEPTIDE BY CO-EXPRESSION OF A BASIC ANTIMICROBIAL PEPTIDE AND AN ACIDIC PEPTIDE USING A TRANSLATIONAL COUPLING SYSTEM

(75) Inventors: Sun Chang Kim, Daejeon (KR); Su A Jang, Daejeon (KR); Bong Hyun Sung, Daejeon (KR); Jung Min Kim, Daejeon (KR); Ki Jung Lim, Daejeon (KR); Ju Ri Shin, Daejeon (KR); Ju Young Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 211 days.

(21) Appl. No.: 12/313,513

(22) Filed: Nov. 19, 2008

(65) Prior Publication Data
US 2010/0184949 A1    Jul. 22, 2010

(30) Foreign Application Priority Data

Dec. 31, 2007 (KR) ........................ 10-2007-0141932

(51) Int. Cl.
*C12P 21/06* (2006.01)
*C12P 21/04* (2006.01)
(52) U.S. Cl. .................... 435/69.1; 435/71.1; 435/71.2; 435/71.3
(58) Field of Classification Search .......................... None
See application file for complete search history.

(56) References Cited

U.S. PATENT DOCUMENTS 5,340,725 A * 8/1994 Ueda et al. .................. 435/69.4

FOREIGN PATENT DOCUMENTS

KR         10-0314721         1/2001

OTHER PUBLICATIONS

Jang et al., "Direct Expression of Antimicrobial Peptides in an Intact Form by a Translationally Coupled Two-Cistron Expression System", Appl. Environmen. Microbiol. 75:3980-3986, 2009.*
Lee et al. "Enhanced expression of tandem multimers of the antimicrobial peptide buforin II in *Escherichia coli* by the DEAD-box protein and trxB mutant", Appl. Microbiol. Biotechnol. 58:790-796, 2002.*
Park et al., "Structure-activity analysis of buforin II, a histone H2A-derived antimicrobial peptide: The proline hinge is responsible for the cell-penetrating ability of buforin II", Proc. Natl. Acad. Sci. 97:8245-8250, 2000.*
Lee et al. "Acidic Peptide-Mediated Expression of the Antimicrobial Peptide Buforin II as Tandem Repeats in *Escherichia coli*", Prot. Exp. Purif. 12:53-60, 1998.*
Saito et al., "Direct Expression of a Synthetic Somatomedin C Gene in *Escherichia coli* by Use of a Two-Cistron System", J. Biochem. 101:1281-1288, 1987.*
Smith et al., "Generating a synthetic genome by whole genome assembly: øX174 bacteriophage from synthetic oligonucleotides" PNAS, Dec. 23, 2003, vol. 100, No. 26, pp. 15440-15445.

* cited by examiner

*Primary Examiner* — David J Steadman
(74) *Attorney, Agent, or Firm* — Christie, Parker & Hale, LLP (57) ABSTRACT

The present invention relates to a gene construct which is capable of achieving efficient production of an antimicrobial peptide in a microorganism, and a method for efficient mass production and separation of an antimicrobial peptide using the same. The gene construct of the present invention has a translationally coupled configuration of two independent and separate cistrons which encode an acidic peptide and a basic antimicrobial peptide, each having an opposite charge, under the control of a single promoter. The translationally coupled acidic peptide and basic antimicrobial peptide undergo charge-charge interaction simultaneously with expression thereof to neutralize the potential cytotoxicity of the antimicrobial peptide, resulting in prevention of antimicrobial peptide-mediated killing of host microorganisms. In addition, a conjugate of the acidic peptide and the antimicrobial peptide can be separated without chemical or enzymatic treatment. Therefore, it is possible to achieve easy mass production of antimicrobial peptides from recombinant microorganisms.

5 Claims, 6 Drawing Sheets

FIG. 1a

SEQ ID NO: 1 a. mIF1 sequence (150 amino acids)

| 1   | tgt | tac | tgc | tgt | gac | cca | tgt | gta | aaa | gaa | gca | gaa | aac | ctt | aag | 45  |
|-----|-----|-----|-----|-----|-----|-----|-----|-----|-----|-----|-----|-----|-----|-----|-----|-----|
| 1   | C   | Y   | C   | Q   | D   | P   | Y   | V   | K   | E   | A   | E   | N   | L   | K   | 15  |
| 46  | aaa | tat | ttt | aat | gca | ggt | cat | tca | gat | gta | gcg | gat | aat | gga | act | 90  |
| 16  | K   | Y   | F   | N   | A   | G   | H   | S   | D   | V   | A   | D   | N   | G   | T   | 30  |
| 91  | ctt | ttc | tta | ggc | att | ttg | aag | aat | tgg | aaa | gag | gag | agt | gac | aga | 135 |
| 31  | L   | F   | L   | G   | I   | L   | K   | N   | W   | K   | E   | E   | S   | D   | R   | 45  |
| 136 | aaa | tat | atg | cag | agc | caa | att | gtc | tcc | ttt | tac | ttc | aaa | ctt | ttt | 180 |
| 46  | K   | I   | M   | Q   | S   | Q   | I   | V   | S   | F   | Y   | F   | K   | L   | F   | 60  |
| 181 | aaa | aac | ttt | aaa | gat | gac | cag | agc | atc | caa | aag | agt | gtg | gag | acc | 225 |
| 61  | K   | N   | F   | K   | D   | D   | Q   | S   | I   | Q   | K   | S   | V   | E   | T   | 75  |
| 226 | atc | aag | gaa | gac | atg | aat | gtc | aag | ttt | ttc | aat | agc | aac | aaa | aag | 270 |
| 76  | I   | K   | E   | D   | M   | N   | V   | K   | F   | F   | N   | S   | N   | K   | K   | 90  |
| 271 | aaa | cga | gat | gac | ttc | gaa | aag | ctg | act | aat | tat | tcg | gta | act | gac | 315 |
| 91  | K   | R   | D   | D   | F   | E   | K   | L   | T   | N   | Y   | S   | V   | T   | D   | 105 |
| 316 | ttg | aat | gtc | caa | cgc | aaa | gca | ata | cat | gaa | ctc | atc | caa | gtg | atg | 360 |
| 106 | L   | N   | V   | Q   | R   | K   | A   | I   | H   | E   | L   | I   | Q   | V   | M   | 120 |
| 361 | gct | gaa | ctg | tcg | cca | gca | gct | aaa | aca | ggg | aag | cga | aaa | agg | agt | 405 |
| 121 | A   | E   | L   | S   | P   | A   | A   | K   | T   | G   | K   | R   | K   | R   | S   | 135 |
| 406 | cag | atg | ctg | ttt | cga | ggt | cga | aga | gca | tcc | cag | gag | gag | gtg | gaa | 450 |
| 136 | Q   | M   | L   | F   | R   | G   | R   | R   | A   | S   | Q   | E   | E   | V   | E   | 150 |
| 451 | taa | 453 |     |     |     |     |     |     |     |     |     |     |     |     |     |     |
| 151 | *   |     |     |     |     |     |     |     |     |     |     |     |     |     |     |     |

FIG. 1b

SEQ ID NO: 2 b. mIF2 sequence (92 amino acids)

| 1   | tgt | tac | tgc | tgt | gac | cca | tgt | gta | aaa | gaa | gca | gaa | aac | ctt | aag | 45  |
|-----|-----|-----|-----|-----|-----|-----|-----|-----|-----|-----|-----|-----|-----|-----|-----|-----|
| 1   | C   | Y   | C   | Q   | D   | P   | Y   | V   | K   | E   | A   | E   | N   | L   | K   | 15  |
| 46  | aaa | tat | ttt | aat | gca | ggt | cat | tca | gat | gta | gcg | gat | aat | gga | act | 90  |
| 16  | K   | Y   | F   | N   | A   | G   | H   | S   | D   | V   | A   | D   | N   | G   | T   | 30  |
| 91  | ctt | ttc | tta | ggc | att | ttg | aag | aat | tgg | aaa | gag | gag | agt | gac | aga | 135 |
| 31  | L   | F   | L   | G   | I   | L   | K   | N   | W   | K   | E   | E   | S   | D   | R   | 45  |
| 136 | aaa | tat | atg | cag | agc | caa | att | gtc | tcc | ttt | tac | ttc | aaa | ctt | ttt | 180 |
| 46  | K   | I   | M   | Q   | S   | Q   | I   | V   | S   | F   | Y   | F   | K   | L   | F   | 60  |
| 181 | aaa | aac | ttt | aaa | gat | gac | cag | agc | atc | caa | aag | agt | gtg | gag | acc | 225 |
| 61  | K   | N   | F   | K   | D   | D   | Q   | S   | I   | Q   | K   | S   | V   | E   | T   | 75  |
| 226 | atc | aag | gaa | gac | atg | aat | gtc | aag | ttt | ttc | aat | agc | aac | gag | gag | 270 |
| 76  | I   | K   | E   | D   | M   | N   | V   | K   | F   | F   | N   | S   | N   | E   | E   | 90  |
| 271 | gtg | gaa | taa | 279 |     |     |     |     |     |     |     |     |     |     |     |     |
| 91  | V   | E   | *   | 92  |     |     |     |     |     |     |     |     |     |     |     |     |

FIG. 1c

SEQ ID NO: 3 c. mIF3 sequence (63 amino acids)

| 1   | tgt | tac | tgc | tgt | gac | cca | tgt | gta | aaa | gaa | gca | gaa | aac | ctt | aag | 45  |
|-----|-----|-----|-----|-----|-----|-----|-----|-----|-----|-----|-----|-----|-----|-----|-----|-----|
| 1   | C   | Y   | C   | Q   | D   | P   | Y   | V   | K   | E   | A   | E   | N   | L   | K   | 15  |
| 46  | aaa | tat | ttt | aat | gca | ggt | cat | tca | gat | gta | gcg | gat | aat | gga | act | 90  |
| 16  | K   | Y   | F   | N   | A   | G   | H   | S   | D   | V   | A   | D   | N   | G   | T   | 30  |
| 91  | ctt | ttc | tta | ggc | att | ttg | aag | aat | tgg | aaa | gag | gag | agt | gac | aga | 135 |
| 31  | L   | F   | L   | G   | I   | L   | K   | N   | W   | K   | E   | E   | S   | D   | R   | 45  |
| 136 | aaa | ata | atg | cag | agc | caa | att | gtc | tcc | ttt | tac | ttc | aaa | ctt | gag | 180 |
| 46  | K   | I   | M   | Q   | S   | Q   | I   | V   | S   | F   | Y   | F   | K   | L   | E   | 60  |
| 181 | gag | gtg | gaa | taa | 192 |     |     |     |     |     |     |     |     |     |     |     |
| 61  | E   | V   | E   | *   | 63  |     |     |     |     |     |     |     |     |     |     |     |

FIG. 2a

SEQ ID NO: 6 a.histonin II sequence (21 amino acids)

```
1    cgt gct ggt ctg cag ttc ccg gtt ggt cgt ctg ctg cgt cgt ctg    45
1     R   A   G   L   Q   F   P   V   G   R   L   L   R   R   L    15

46   ctg cgt cgt ctg ctg cgt taa    66
16    L   R   R   L   L   R   *     21
```

FIG. 2b

DNA construct for translational coupling of acidic peptide and antimicrobial peptide gene of acidic co-expression protein | gene of antimicrobial peptide

SEQ ID NO: 5

AGGAGGT: Shine Dalgarno seqeunce

METHOD FOR THE MASS EXPRESSION OF AN ANTIMICROBIAL PEPTIDE BY CO-EXPRESSION OF A BASIC ANTIMICROBIAL PEPTIDE AND AN ACIDIC PEPTIDE USING A TRANSLATIONAL COUPLING SYSTEM

CROSS-REFERENCE TO RELATED APPLICATION

This application claims priority of Korean Patent Application Number 10-2007-0141932, filed on Dec. 31, 2007.

INCORPORATION BY REFERENCE

The material in the text file entitled "12313513SEQLISTING," amended Feb. 2, 2011 and being 7,170 bytes in size, is herein incorporated by reference in its entirety.

BACKGROUND OF THE INVENTION

1. Field of the Invention

The present invention relates to a gene construct which is capable of achieving efficient production of an antimicrobial peptide in a microorganism, and a method for efficient mass production and separation of an antimicrobial peptide using the same.

2. Description of the Related Art

Antimicrobial peptides exhibit an antimicrobial activity through characteristic action mechanisms which are distinctly different from those of conventional antibiotics suffering from problems of microbial resistance, and are therefore advantageous in terms of the low risk of a microbial drug resistance. For this reason, the antimicrobial peptides have a potential of high industrial applicability in fields of pharmaceutical and food industry as they may be used as promising next-generation antibiotic substances.

However, there is a great obstacle to industrial applications of antimicrobial peptides, since conventional peptide production techniques do not permit industrial-scale production of the desired peptides at low production costs. For example, production of antimicrobial peptides by chemical synthesis is economically inefficient. Genetic engineering techniques employing microorganisms allow production of antimicrobial peptides in an economical manner, but suffer from shortcomings associated with high susceptibility of the produced peptides to breakage by the attack of a variety of microbial host proteases because most of the antimicrobial peptides are short peptides consisting of only 10 to 40 amino acid residues. Additionally, antimicrobial activity of the expressed antimicrobial peptides suppresses growth of host microorganisms, which disadvantageously results in a very low production yield of desired peptides.

Requirements for mass expression and production of antimicrobial peptides in microorganisms are as follows. First, it is important to ensure that antimicrobial peptides are not readily decomposed by the attack of host microorganism proteases. Second, it is necessary to effectively neutralize toxicity of antimicrobial peptides on microorganisms. Conventional methods have been usually conducted using a fusion protein to produce a desired peptide from host microorganisms without causing death of host cells. However, this method disadvantageously requires separation of a desired antimicrobial peptide from the fusion protein using protease (such as Factor Xa or enterokinase) or a chemical agent (such as cyanogen bromide (CNBr) or hydroxylamine). That is, separation of the desired peptide from the fusion protein is a time-consuming and energy-intensive process, which leads to a significant decrease in the expression yield of peptide as well as a fatal disadvantage associated with unwanted residues remaining between the fusion protein and the antimicrobial peptide even after separation of the desired peptide is complete.

SUMMARY OF THE INVENTION

Therefore, the present invention has been made in view of the above problems, and it is an object of the present invention to provide a method which is capable of achieving convenient and efficient mass production of an antimicrobial peptide without causing complexity of a procedure used in separation of a fusion partner and an antimicrobial peptide and loss of productivity, upon fusion expression of the antimicrobial peptide in microorganisms.

It is another object of the present invention to provide a gene construct for mass production of an antimicrobial peptide.

It is yet another object of the present invention to provide a fusion partner of an antimicrobial peptide.

As a result of a variety of extensive and intensive studies and experiments to solve the problems as described above, the present inventors succeeded in developing a method for mass production of an antimicrobial peptide by neutralizing toxic effects of the antimicrobial peptide on a host microorganism, via the formation of an inclusion body through co-expression of the antimicrobial peptide and an acidic peptide having opposite charges capable of neutralizing charges of the antimicrobial peptide using a translationally coupled bicistronic system.

In accordance with an aspect of the present invention, the above and other objects can be accomplished by the provision of a method for producing an antimicrobial peptide, comprising:

(i) preparing a bicistronic DNA construct for translationally coupled expression of a gene of a basic antimicrobial peptide and a gene of an acidic peptide into each separate peptide under the control of a single promoter, wherein the acidic peptide is capable of substantially neutralizing positive charges of the basic antimicrobial peptide;

(ii) inserting the bicistronic DNA construct into an expression vector and introducing the expression vector into a microorganism to express an inclusion body of the basic antimicrobial peptide and the acidic peptide; and (iii) recovering the inclusion body from the microorganism and separating the basic antimicrobial peptide from the inclusion body based on charge differences.

In one embodiment of the present invention, two cistrons of the DNA construct are connected in the form of a UAAUG or UGAUG sequence (corresponding to TAATG or TGATG in the DNA construct) where a termination codon UAA or UGA of a first cistron is overlapped with an initiation codon AUG of a second cistron.

In one embodiment of the present invention, the constructing step of the DNA construct may include introducing a base sequence containing a Shine-Dalgarno sequence (AGGAGGT) in front of the termination codon of the first cistron, in order to enhance translation of the second cistron.

In another embodiment of the present invention, the basic antimicrobial peptide may be any one of histonin II, parasin and pexiganan.

In another embodiment of the present invention, the acidic peptide may have one or more disulfide bonds.

In another embodiment of the present invention, the acidic peptide may be any one of mIF1 having an amino acid sequence of SEQ ID NO: 1, mIF2 having an amino acid sequence of SEQ ID NO: 2 and mIF3 having an amino acid sequence of SEQ ID NO: 3.

In accordance with another aspect of the present invention, there is provided a bicistronic DNA construct for translationally coupled expression of a gene of a basic antimicrobial peptide and a gene of an acidic peptide into each separate peptide under the control of a single promoter, wherein the acidic peptide is capable of substantially neutralizing positive charges of the basic antimicrobial peptide.

In one embodiment of the present invention, the acidic peptide capable of substantially neutralizing positive charges of the basic antimicrobial peptide may be any one of an mIF1 peptide having an amino acid sequence of SEQ ID NO: 1, an mIF2 peptide having an amino acid sequence of SEQ ID NO: 2 and an mIF3 peptide having an amino acid sequence of SEQ ID NO: 3.

BRIEF DESCRIPTION OF THE DRAWINGS

FIG. 1 shows amino acid sequences of acidic co-expression partner proteins.

FIG. 2 schematically shows a DNA fragment for translationally coupled bicistronic expression of an antimicrobial peptide and an acidic protein.

DETAILED DESCRIPTION OF THE PREFERRED EMBODIMENTS

Hereinafter, the present invention will be described in more detail.

A bicistronic expression system used in the present invention is a system capable of providing co-expression of two different genes under the control of a single promoter. For example, multi-cistronic expression of genes is frequently found in various prokaryotes in nature. Based on application and modification of such a prokaryotic multi-cistronic expression system, the present inventors have developed a translationally coupled bicistronic expression system for efficient mass expression of an antimicrobial peptide which is difficult to achieve the sole expression thereof.

More specifically, the present inventors have developed a system which is capable of achieving mass expression of the antimicrobial peptide by attenuating or counteracting cytotoxicity caused by the attack of strong basicity of the antimicrobial peptide on host DNAs or RNAs, that is, by transiently neutralizing strong basicity of the antimicrobial peptide.

For this purpose, a co-expression partner is introduced to elicit translationally coupled expression of the antimicrobial peptide and the co-expression partner under the control of a single promoter.

There is no particular limit to the antimicrobial peptide that can be used in the bicistronic expression system of the present invention, so long as it is a basic antimicrobial peptide. Preferred examples of the basic antimicrobial peptide may include histonin II, parasin, and pexiganan. More preferred is histonin II.

The co-expression partner in the bicistronic expression system of the present invention must have acidic charges that can neutralize basicity of the antimicrobial peptide to transiently attenuate the cytotoxicity thereof. Additionally, in order to prevent the cytotoxicity of the product on the host and effectively augment the productivity, the antimicrobial peptide should be expressed and produced in an insoluble form. For these reasons, the co-expression partner is employed which has acidic (negative) charges while simultaneously being capable of effectively forming a large amount of inclusion bodies.

The co-expression peptide is co-expressed with the antimicrobial peptide under the control of a single promoter and is expressed in a translational coupling manner, not in a fusion expression manner. That is, the co-expression peptide and the antimicrobial peptide each have a translational initiation region (TIR), and are expressed in a manner that translation of the co-expression protein undergoing preceding expression intimately affects translation of the antimicrobial peptide entering following expression (see FIG. 3).

Two cistrons, expression of which is under the control of a single promoter, are used in the present invention. The strongly basic antimicrobial peptide that is a target to be expressed is placed on a second cistron, and the acidic peptide is placed on a first cistron to neutralize the target antimicrobial peptide. Then, the first cistron and the second cistron are connected in a manner that a termination codon of the first cistron partially overlaps with an initiation codon of the second cistron (resulting in translational coupling of two cistrons). Preferably, two cistrons are connected in the form of a UAAUG or UGAUG sequence which is an overlapping of the termination codon UAA or UGA of the first cistron with the initiation codon AUG of the second cistron. More preferably, the first cistron and the second cistron are connected in an overlapping fashion of UAAUG (corresponding to TAATG in the DNA construct). The configuration of such an overlapping base sequence enables successive expression of two cistrons. That is, an expression process is continuously carried out using a new initiation codon of the second cistron before the ribosome used in translation of the first cistron is dissociated from mRNA by a termination release factor (TRF) to result in termination of translation. As a result, successive expression of two cistrons enables conjugation of two peptides which were expressed in a proximate distance.

In order to further enhance an expression level of the second cistron, more efficient binding of a ribosome to mRNA can be achieved by configuring the bicistronic expression system to contain a Shine-Dalgarno sequence (AGGAGGT) before a 3-7 base sequence of the termination codon of the first cistron, i.e., before 5-9 bases of the initiation codon of the second cistron. For example, a sequence containing Shine-Dalgarno sequence may be a sequence of NAGGAGGTNNNN (N: any one of A, C, T and G) (SEQ ID NO: 4). Preferably, the GAGGAGGTGGAA sequence (SEQ ID NO:

5) that encodes an amino acid sequence of EEVE (SEQ ID NO: 20) contains a perfect Shine-Dalgarno sequence AGGAGGT. In addition, the presence of three amino acid residues E (glutamic acid) contributes to a negative charge value of −3 to thereby provide an optimal sequence for neutralization of the basic antimicrobial peptide.

The acidic peptide that can be used in the present invention may be artificially designed or otherwise may be appropriately selected from naturally-occurring acidic peptides. In addition, a gene encoding the acidic peptide may be chemically synthesized or isolated from nature. In one embodiment of the present invention, a preferred acidic peptide is an analogue or fragment of a human interferon-gamma (hIFN-γ).

In order to prevent binding of the antimicrobial peptide to DNA or RNA molecules, an acidic peptide is designed to neutralize positive charges of the basic antimicrobial peptide. Preferred is an acidic peptide that is capable of substantially neutralizing positive charges of the antimicrobial peptide. Even though a length of the acidic peptide is not critical, a shorter one is favorable for production efficiency of the antimicrobial peptide. Taking into account the number and distribution of positive charges of the antimicrobial peptide to be expressed, preferred is an acidic peptide having the number and distribution of negative charges suitable for effective neutralization of positive charges.

More preferably, the acidic peptide has at least two cysteine residues. Following expression of the peptide, these cysteine residues are putatively believed to facilitate the charge-charge interaction between negative charges of the acidic peptide and positive charges of the antimicrobial peptide by taking part in the formation of a secondary structure via a disulfide bond. In addition, the acidic peptide is preferably a peptide having acidity capable of neutralizing basicity of the antimicrobial peptide, in conjunction with capability to form an inclusion body. This is because formation of the inclusion body can prevent degradation of the peptide that may occur by the attack of host proteases.

In an embodiment of the present invention, the acidic peptide may have preferably 2, 3, 4, 5, 6, 7, 8, 9 or 10 cysteine residues. Increasing numbers of the cysteine residues exhibit a higher tendency to form the inclusion body.

In summary, depending on the kinds of the antimicrobial peptides, the relevant acidic peptide may be designed and selected according to the following criteria. That is, the acidic peptide should have or exhibit: (1) the number and distribution of negative charges similar to the number and distribution of positive charges of the desired antimicrobial peptide, (2) at least two cysteine residues while having a cysteine residue on the amino terminus, (3) expression capacity in the form of an insoluble inclusion body, such that a peptide of interest can be stable against the attack of microbial proteases, and (4) shorter peptide length for efficient production of the antimicrobial peptide.

As the host microorganism used in the present invention, a variety of microorganisms can be used which are capable of achieving low-cost, high-productivity of recombinant proteins due to feasibility of easy genetic manipulation. Examples of the host microorganism that can be used in the present invention may include bacteria (such as E. coli, Bacillus subtilis, etc.), yeast, and the like. Preferred is E. coli.

A vector suited for introduction of the bicistronic DNA construct of the present invention into a target microorganism can be easily selected by those skilled in the art, depending on the kinds of host microorganisms, sizes of peptides, etc. Further, it is to be understood that insertion of the DNA construct of the present invention into a proper expression vector and subsequent introduction of the DNA construct-carrying expression vector into the host microorganism can be easily practiced by those skilled in the art.

The acidic protein and the antimicrobial peptide expressed in the form of an inclusion body are independently expressed followed by conjugation, instead of being expressed in the form of a fusion protein. Accordingly, there is no need for separation of the desired product using proteases (such as Factor Xa or enterokinase) or chemicals (such as CNBr or hydroxylamine). That is, it is possible to easily separate the desired peptide product based on the charge difference, after the inclusion body is dissolved. In one embodiment of the present invention, easy separation of the desired product can be achieved by means of an ion-exchange column.

EXAMPLES

Now, the present invention will be described in more detail with reference to the following Examples. These examples are provided only for illustrating the present invention and should not be construed as limiting the scope and spirit of the present invention. In particular, specific antimicrobial peptides, acidic peptides, DNA constructs, primers, host microorganisms, vectors, separation and purification methods, etc., exemplified in Examples of the present invention are only preferred embodiments. Therefore, it should be understood that any invention using translational coupling systems for co-expression of the acidic peptide upon mass production of various basic antimicrobial peptides fall within the scope of the present invention.

Example 1

Amino Acid Sequencing of Acidic Proteins and Construction of Acidic Protein-Encoding Genes For expression of histonin II (amino acid sequence: RAGLQFPVGRLLRRLLRRLLR) (SEQ ID NO: 6) that is a potent antimicrobial peptide having an amino acid sequence identical with a peptide of SEQ ID NO: 15 disclosed in Korean Patent No. 0314721, assigned to the present applicant and entitled "BIOLOGICALLY ACTIVE PEPTIDES", acidic peptide candidates having the following characteristics were screened taking into consideration the charge distribution of histonin II:

1. Number and distribution of negative charges similar to the number and distribution of positive charges of histonin II,
2. Cysteine residue on the amino terminus,
3. Expression capacity in the form of an insoluble inclusion body, such that a peptide of interest can be stable against the attack of microbial proteases, and
4. Shorter peptide length for efficient production of an antimicrobial peptide.

Figure 1A:
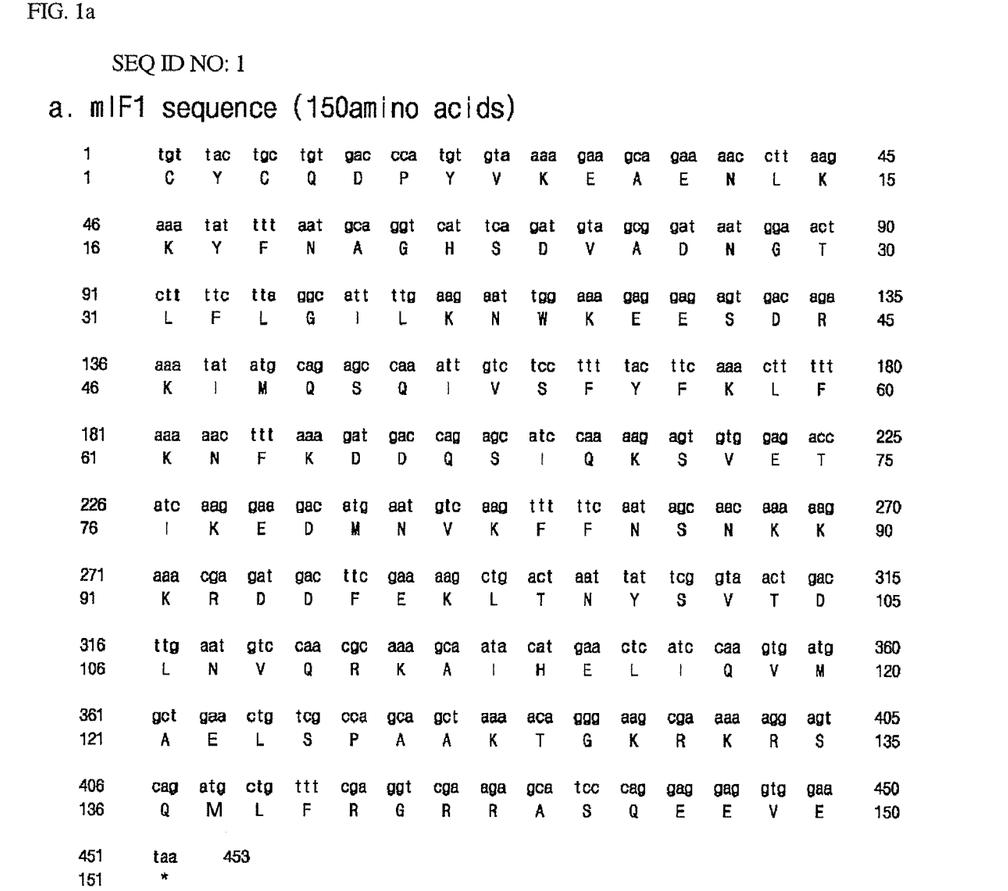
FIG. 1a depicts an amino acid sequence of mIF1.

For translational coupling of an antimicrobial peptide with each of the screened acidic proteins, an NdeI recognition site (CATATG) for cloning was introduced at the amino terminus of a co-expression protein. In order to further increase acidity (negativity) of the co-expression acidic protein and elicit better translation of the second cistron, the carboxyl terminus was provided with the introduction of a base sequence GAG-GAGGTGGAA (SEQ ID NO: 5) (encoding an amino acid EEVE) (SEQ ID NO: 20) containing a Shine-Dalgarno sequence (AGGAGGT) before the termination codon (see FIG. 1a).

Step 1

A human interferon-gamma (hIFN-γ) is a protein consisting of 146 amino acid residues. When hIFN-γ is over-expressed in E. coli, more than 90% of the total protein forms an insoluble inclusion body. Due to having acidity and cysteine residue(s) close to the amino terminus, hIFN-γ is favorable as the co-expression acidic protein. The carboxyl terminus of hIFN-γ was modified to contain an intercistronic region, thus rendering hIFN-γ to have an acidic charge value of −5. Various kinds of single-stranded oligonucleotides (SEQ ID NOs: 7-11 as listed in Table 1) were synthesized to encode hIFN-γ, and a double-stranded DNA fragment of the co-expression protein mIF1 consisting of 150 amino acid residues (FIG. 1a)(SEQ ID NO: 1) was constructed by recombinant PCR (Smith H.O. et. al., Proc. Natl. Acad. Sci. USA, 2003, 100(26) 15440-15445).

Figure 1B:
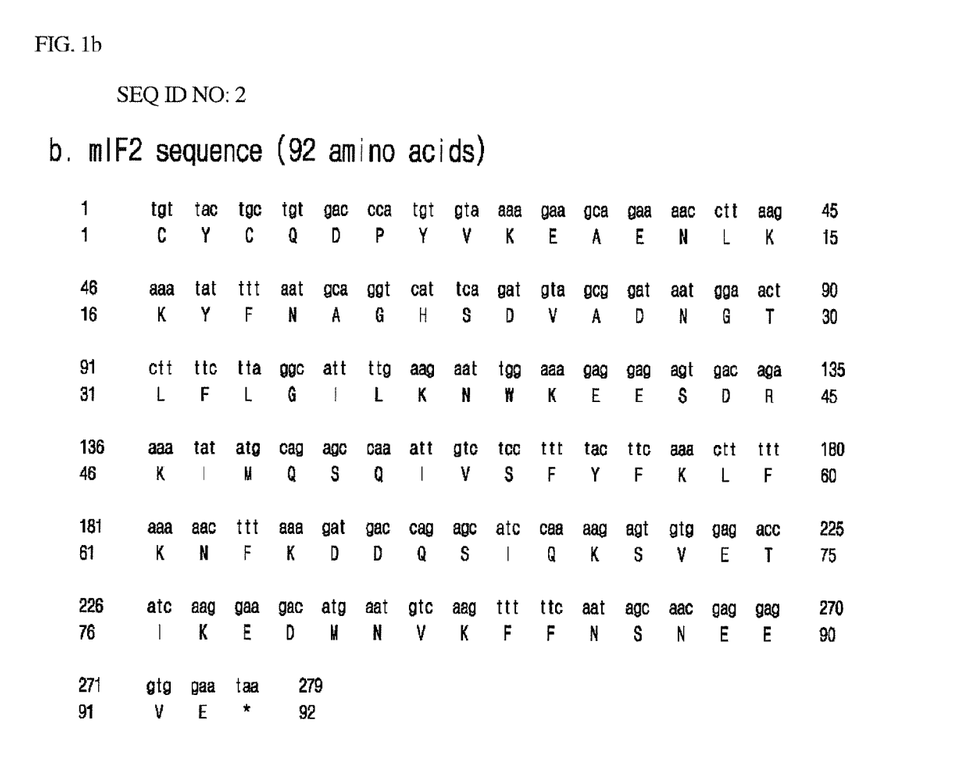
FIG. 1b depicts an amino acid sequence of mIF2.

Step 2 hIFN-γ presented in Step 1 has a molecular weight approximately 7-times greater than that of an antimicrobial peptide to be expressed, so there is a need for a smaller co-expression protein for effective mass production of the antimicrobial peptide. An intercistronic region (coding for an amino acid EEVE) (SEQ ID NO: 20) was added to an 88 a.a. protein at the amino terminus of hIFN-γ to thereby construct mIF2 consisting of 92 amino acid residues and having an acidic charge value of −6. Using single-stranded oligonucleotides (SEQ ID NOs: 7 to 11 as listed in Table 1), a double-stranded DNA fragment of the co-expression protein mIF2 consisting of 92 amino acid residues (FIG. 1b) (SEQ ID NO: 2) was constructed by recombinant PCR.

Step 3

Figure 1C:
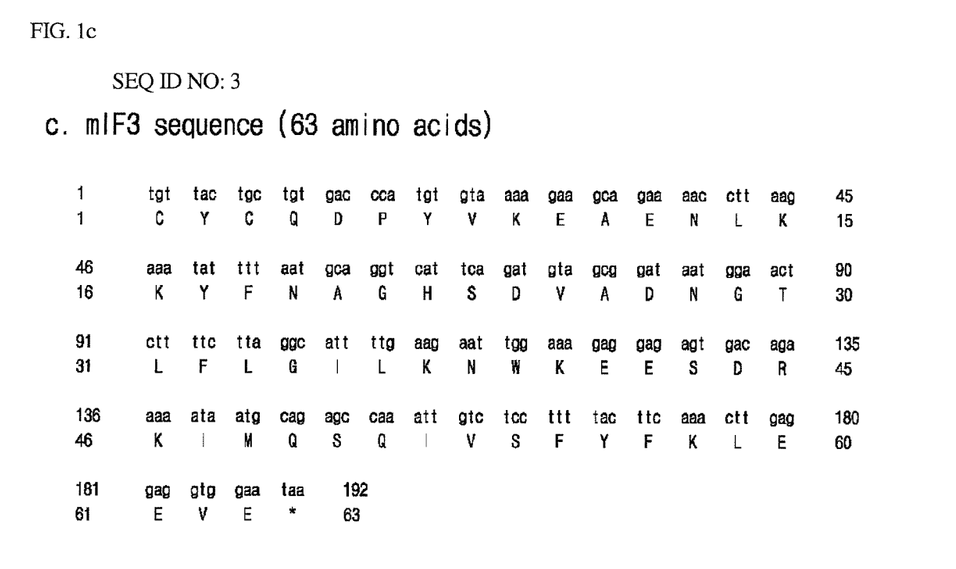
FIG. 1c depicts an amino acid sequence of mIF3.

To construct a hIFN-γ analogue shorter than that of Step 2, an intercistronic region (encoding an amino acid EEVE) (SEQ ID NO: 20) was added to a 59 a.a. protein at the amino terminus of hIFN-γ to thereby construct mIF3 consisting of 63 amino acid residues and having an acidic charge value of −6. Using single-stranded oligonucleotides (SEQ ID NOs: 7-9 as listed in Table 1), a double-stranded DNA fragment of the co-expression protein mIF3 consisting of 63amino acid residues (FIG. 1c)(SEQ ID NO: 3) was constructed by recombinant PCR.

TABLE 1

Primers for preparing translationally coupled DNA constructs

| No | Sequences 5'--> 3' | Primers |
|---|---|---|
| 1 | TGTTACTGCCAGGACCCATATGTAAAAGAAG CAGAAAACCTTAAGAAATATTTTAATGCAGG TCATTCAGATGTAGCGGA | mIF1 synthesis 1 (80mer) (SEQ ID NO: 7), |
| 2 | ATGTCCTCGTCACTCTCCTCTTTCCAATTCT TCAAAATGCCTAAGAAAAGAGTTCCATTATC CGCTACATCTGAATGACC | mIF1 synthesis 2 (80mer) (SEQ ID NO: 8), |
| 3 | GAGGAGAGTGACGAGGACATAATGCAGAGCC AAATTGTCTCCTTTTACTTCAAACTTTTTAA AAACTTTAAAGATGACCA | mIF1 synthesis 3 (80mer) (SEQ ID NO: 9), |
| 4 | CTATTGAAAAACTTGACATTCATGTCTTCCT TGATGGTCTCCACACTCTTTTGGATGCTCTG GTCATCTTTAAAGTTTTT | mIF1 synthesis 4 (80mer) (SEQ ID NO: 10), |
| 5 | AATGTCAAGTTTTTCAATAGCAACAAAAAGA AACGAGATGACTTCGAAAAGCTGACTAATTA TTCGGTAACTGACTTGAA | mIF1 synthesis 5 (80mer) (SEQ ID NO: 11), |
| 6 | GCTGCTGGCGACAGTTCAGCCATCACTTGGA TGAGTTCATGTATTGCTTTGCGTTGGACATT CAAGTCAGTTACCGAATA | mIF1 synthesis 6 (80mer) (SEQ ID NO: 12), |

TABLE 1-continued

Primers for preparing translationally coupled DNA constructs

| No | Sequences 5'--> 3' | Primers |
|---|---|---|
| 7 | GCTGAACTGTCGCCAGCAGCTAAAACAGGGG AAGACGAGGATAGTCAGATGCTGTTTCGAGG TCGAAGAGCATCCCAG | mIF1 synthesis 7 (80mer) (SEQ ID NO: 13), |
| 8 | GGAATTCCATATGTGTTACTGCCAGGACCCA | mIF1 synthesis 8 (31mer) (SEQ ID NO: 14), |
| 9 | CATTATTCCACCTCCTCCTGGGATGCTCTTC GACCTC | mIF1 synthesis 9 (37mer) (SEQ ID NO: 15), |
| 10 | CATTATTCCACCTCCTCGTTGCTATTGAAAA ACTTGAC | mIF2 synthesis 1 (38mer) (SEQ ID NO: 16), |
| 11 | CATTATTCCACCTCCTCAAGTTTGAAGTAAA AGGAGAC | mIF3 synthesis 1 (38mer) (SEQ ID NO: 17), |
| 12 | GAGGAGGTGGAATAATGCGTGCTGGTCTGCA GTTCCCGGTTGGTCGTCTGCTGCGTC | histonin II synthesis 1 (57mer) (SEQ ID NO: 18), |
| 13 | CGGGATCCTCAACGCAGCAGACGACGCAGCA GACGACGCAGCAGACGACC | histonin II synthesis 2 (50mer) (SEQ ID NO: 19), |

Example 2

Figure 2A:
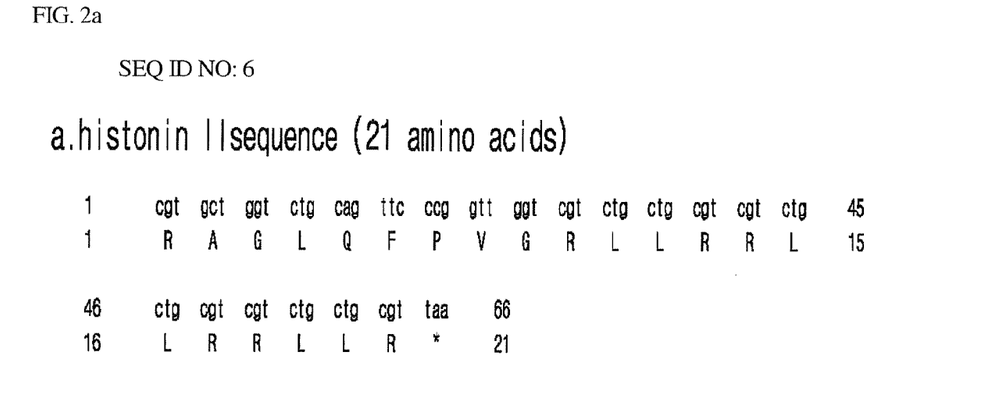
FIG. 2a depicts an amino acid sequence of an antimicrobial peptide histonin

Construction of DNA Fragments for Co-Expression of Antimicrobial Peptides and Acidic Peptides In order to construct a DNA fragment encoding an antimicrobial peptide histonin II gene, single-stranded oligomers were synthesized such as Primers 12 and 13 as set forth in Table 1. Then, a gene fragment encoding double-stranded histonin II was constructed by DNA polymerization (FIG. 2a). Herein, the carboxyl terminus of histonin II was provided with a BamHI recognition site (GGATCC) which will be used upon cloning of histonin II into a vector pET21c.

Figure 2B:
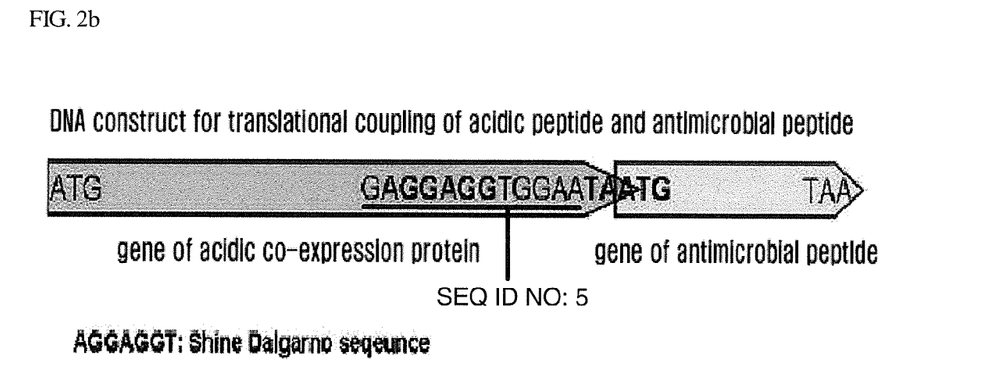
FIG. 2b depicts a DNA fragment for translationally coupled expression of an acidic protein and an antimicrobial peptide.

As shown in FIG. 2b, a DNA fragment for translational coupling of an acidic peptide and an antimicrobial peptide histonin II was constructed by recombinant PCR. In order to construct an mIF1-histonin II (mIF1H) DNA construct where an mIF1 DNA fragment and a histonin II DNA fragment were linked to elicit co-expression thereof, recombinant PCR was carried out using the histonin II double-stranded DNA fragment and the mIF1 DNA fragment of Example 1 as templates and primers (1, 9, and 13)(SEQ ID NOs: 7, 15, and 19) of Table 1. mIF2-histonin II (mIF2H) was constructed by recombinant PCR using the histonin II double-stranded DNA fragment and the mIF2 DNA fragment of Example 1 as templates and primers (1, 10, and 13) (SEQ ID NOs: 7, 16, and 19) of Table 1. Analogously, recombinant PCR was carried out to construct mIF3-histonin II (mIF3H), using the histonin II double-stranded DNA fragment and the mIF3 DNA fragment of Example 1 as templates and primers (1, 11, and 13) (SEQ ID NOs: 7, 16, and 19) of Table 1.

Example 3

Figure 3:
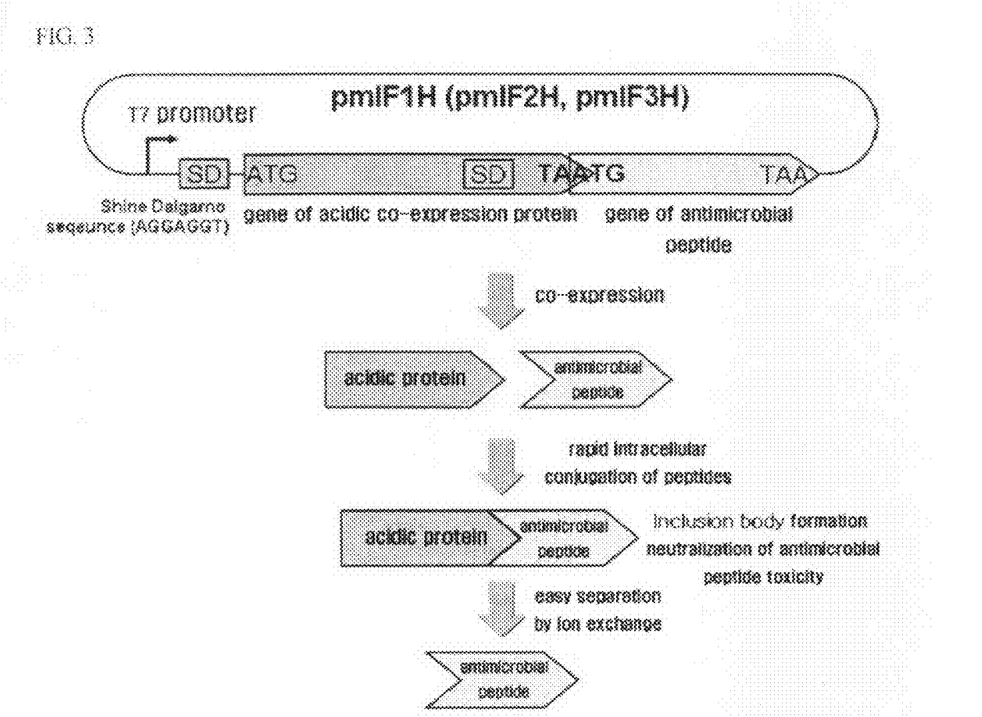
FIG. 3 shows a schematic diagram illustrating the construction strategy of a translationally coupled bicistronic expression vector of acidic protein gene-antimicrobial peptide gene, in conjunction with separation and purification of the desired antimicrobial peptide.

Construction of Translationally Coupled Vector of Acidic Peptide Gene-Antimicrobial Peptide Gene For construction of the acidic peptide gene and the antimicrobial peptide gene synthesized in Examples 1 and 2 into a bicistronic expression vector, a translationally coupled structure was constructed where two cistrons are translationally coupled with each other, but they are independent from each other while being expressed in a state of overlapping with each other, as shown in FIG. 2. As a co-expression partner, an acidic peptide capable of neutralizing a basic antimicrobial peptide and forming an inclusion body was placed in the first cistron. The mIF1H, mIF2H or mIF3H DNA fragment constructed in Example 2 was placed in the second cistron to elicit expression of the antimicrobial peptide. For this purpose, the corresponding DNA fragment mIF1H, mIF2H or mIF3H was cleaved with restriction endonucleases NdeI and BamHI, and a DNA fragment having a desired size was separated using a gel extraction kit (Qiagen, Germany). Then, each of these digested DNA fragments was ligated into NdeI and BamHI sites of the vector pET21c to thereby construct translationally coupled vectors of the acidic peptide and the antimicrobial peptide, pmIF1H, pmIF2H, and pmIF3H, respectively (FIG. 3).

Example 4

Expression Levels of Various Acidic Co-Expression Peptides and Antimicrobial Peptides pmIF1H, pmIF2H and pmIF3H, which were translationally coupled vectors of the acidic peptide with the antimicrobial peptide constructed in Example 3, were each introduced into *E. coli* BL21(DE3) by $CaCl_2$ transformation. *E. coli* strain BL21(DE3) was cultured in a Luria-Bertani (LB) medium containing 1% tryptone, 0.5% yeast extract and 0.5% NaCl. When the culture had reached an $OD_{600}$ of 0.5 to 0.6, 1 mM isopropyl-β-D-thiogalactopyranoside (IPTG) was added to induce peptide expression.

Figure 4:
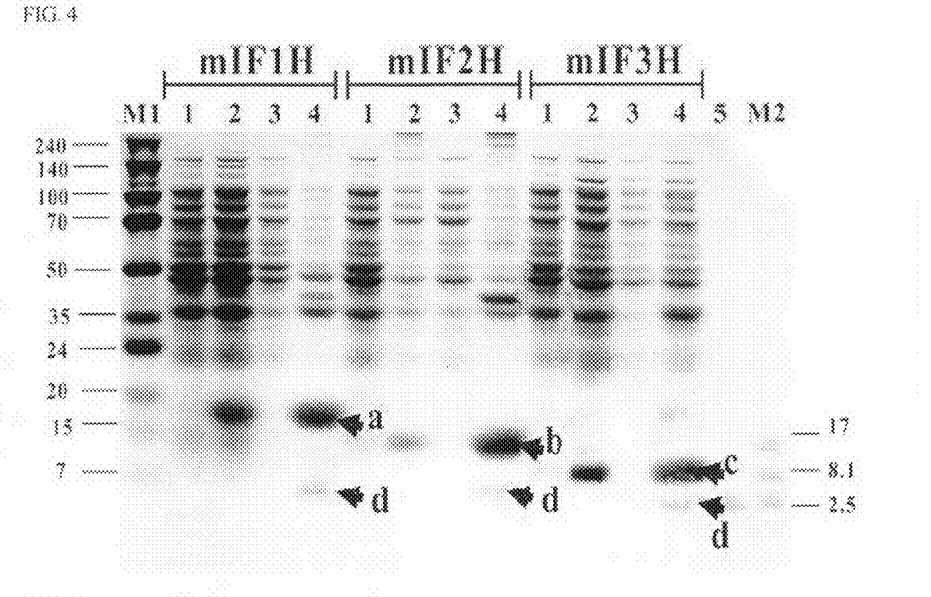
FIG. 4 shows a micrograph comparing expression levels of various acidic co-expression proteins and antimicrobial peptides.

In FIG. 4, M1 and M2 represent a molecular weight standard marker, Lane 1 represents an *E. coli* strain transformed with each of plasmids pmIF1H, pmIF2H and pmIF3H and with no IPTG-induced expression, Lane 2 represents an *E. coli* strain transformed with the plasmid pmIF1H and with IPTG-induced expression, Lane 3 represents a supernatant obtained after cell lysis and centrifugation following IPTG-induced expression, Lane 4 represents a 3M urea solution of a precipitate (inclusion body) obtained after cell lysis and centrifugation, and Lane 5 represents a synthetic antimicrobial peptide as control. Arrows a, b, c, and d represent mIF1 (15.1 kDa), mIF2 (10 kDa), mIF3 (7 kDa), and an antimicrobial peptide (2.5 kDa), respectively.

From co-expression of various acidic peptides and antimicrobial peptides, it was confirmed that introduction of mIF3 with a minimum size consisting of 63 amino acid residues resulted in effective expression of the antimicrobial peptide.

Example 5

Production of Antimicrobial Peptide Histonin II by Translationally Coupled Bicistronic System with Introduction of Optimized Acidic Co-Expression Peptide Using an optimized acidic co-expression peptide mIF3, an antimicrobial peptide was mass-expressed, separated and purified. *E. coli* strain BL21 (DE3) transformed with a vector pmIF3H was grown in 100 mL of an LB medium. When the culture had reached an $OD_{600}$ of 0.5 to 0.6, 1 mM of IPTG was added to induce expression of the desired peptide. The culture was removed 4 hours later, and the cells were disrupted in a Tris buffer solution and centrifuged to obtain a precipitate. The precipitate was dissolved in a 3M urea solution at room temperature for 2 hours and loaded on a 15S Resource cation exchange column, followed by elution with 0.5M NaCl to separate an antimicrobial peptide histonin II. The separated histonin II was purified once more by reverse-phase HPLC with a C-18 column (3.9×300 mm, Millipore), thus recovering a pure peptide.

Figure 5:
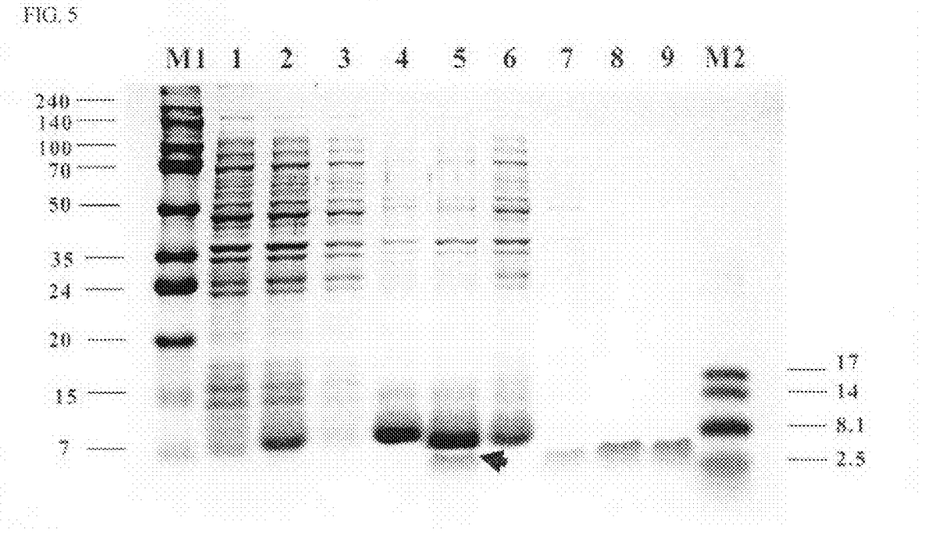
FIG. 5 shows a SDS-PAGE pattern of a peptide solution obtained by pure separation of an antimicrobial peptide histonin II, after IPTG-induced expression of histonin II in *E. coli*.

In FIG. 5, M1 and M2 represent a molecular weight standard marker, Lane 1 represents an *E. coli* strain transformed with the plasmid pmIF3H and with no IPTG-induced expression, Lane 2 represents an *E. coli* strain transformed with the plasmid pmIF3-H and with IPTG-induced expression, Lane 3 represents a sonicated supernatant after IPTG-induced expression, Lane 4 represents a precipitate obtained after sonication, i.e. an insoluble inclusion body, and Lane 5 represents an inclusion body obtained after resolubilization of the precipitate of Lane 4 in 3M urea (pH 10), followed by refolding. Lane 6 and Lane 7 represent samples which were separated by 15S Resource cation chromatography and were each adsorbed or not adsorbed to the column. Lane 8 represents a pure recombinant antimicrobial peptide which was obtained by another reverse-phase HPLC of only the antimicrobial peptide having positive charges in Lane 7. Lane 9 represents a synthetic antimicrobial peptide as control.

When antimicrobial activity of the resulting recombinant antimicrobial peptide was examined, it was confirmed that the recombinant antimicrobial peptide had substantially the same antimicrobial activity as a naturally-occurring antimicrobial peptide.

Example 6

Production of Antimicrobial Peptides Parasin and Pexiganan by Translationally Coupled Bicistronic System with Introduction of Optimized Acidic Co-Expression Peptide From expression of basic antimicrobial peptides parasin and pexiganan other than histonin II using an optimized acidic co-expression peptide mIF3, it was demonstrated that the method of the present invention can be universally applied for the expression of diverse antimicrobial peptides. The *E. coli* strain BL21 (DE3) transformed with each of vectors pmIF3-parasin and pmIF3-pexiganan was grown in 100 mL of an LB medium. When the culture had reached an $OD_{600}$ of 0.5 to 0.6, 1 mM of IPTG was added to induce expression of the desired peptide. The culture was removed 4 hours later, and the cells were disrupted in a Tris buffer solution and centrifuged to obtain a precipitate. The precipitate was dissolved in a 3M urea solution at room temperature for 2 hours and expression levels of the antimicrobial peptides parasin and pexiganan were assayed.

Figure 6:
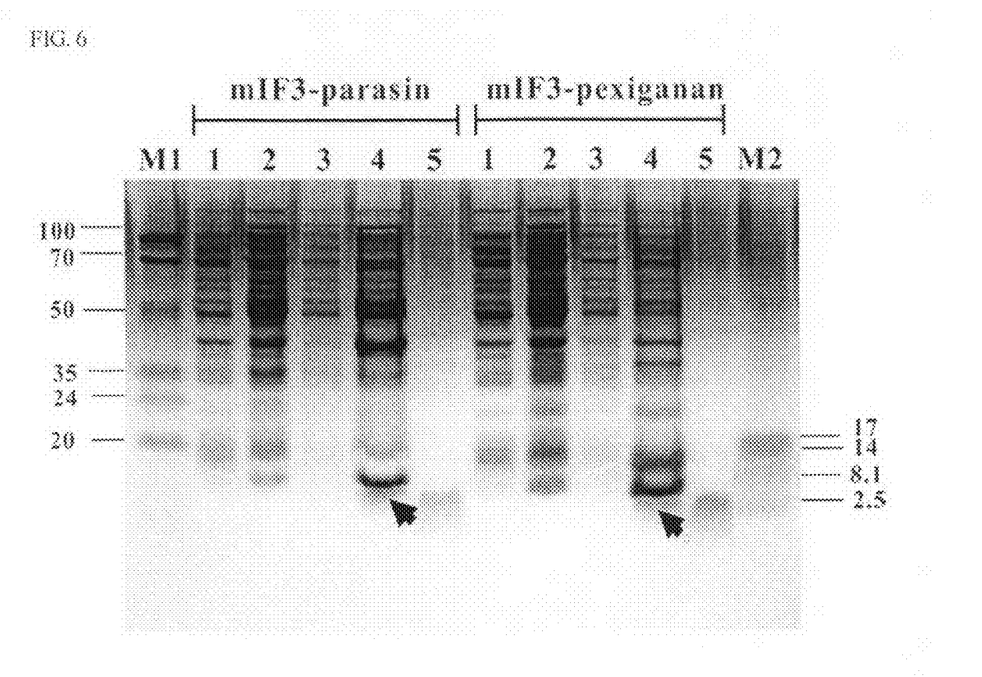
FIG. 6 shows a SDS-PAGE pattern of target peptides after IPTG-induced expression of antimicrobial peptides parasin and pexiganan in *E. coli*.

In FIG. 6, M1 and M2 represent a molecular weight standard marker, Lane 1 represents an *E. coli* strain transformed with each of vectors pmIF3-parasin and pmIF3-pexiganan and with no IPTG-induced expression, Lane 2 represents an *E. coli* strain transformed with each of vectors pmIF3-parasin and pmIF3-pexiganan and with IPTG-induced expression, Lane 3 represents a sonicated supernatant after IPTG-induced expression, Lane 4 represents an inclusion body obtained when an insoluble inclusion body precipitated after sonication was re-solubilized in 3M urea (pH 10), followed by refolding. Lane 5 represents synthetic antimicrobial peptides parasin and pexiganan as controls.

As apparent from the above description, the present invention enables production of a desired peptide by minimizing growth inhibitory effects of antimicrobial peptide expression on a host through translational coupling of an antimicrobial peptide and an acidic protein even without taking an expression system of a desired peptide in the form of a fusion protein. Therefore, it is possible to easily achieve mass production of antimicrobial peptides from recombinant microorganisms, irrespective of the kinds of antimicrobial peptides.

What is claimed is:

1. A method for producing an antimicrobial peptide, comprising:
   (i) preparing a bicistronic DNA construct having a first cistron and a second cistron, wherein the first cistron comprises a gene encoding an acidic peptide and the second cistron comprises a gene encoding a basic antimicrobial peptide, wherein the expression of each gene is under the control of a single promoter, wherein the first cistron comprises the nucleotide sequence of SEQ ID NO:5 immediately 5' to a termination codon of the first cistron, and wherein the acidic peptide is capable of substantially neutralizing positive charges of the basic antimicrobial peptide;
   (ii) inserting the bicistronic DNA construct into an expression vector and transforming a microorganism with the expression vector to express the basic antimicrobial peptide and the acidic peptide as an inclusion body; and
   (iii) recovering the inclusion body from the microorganism and separating the basic antimicrobial peptide from the acidic peptide based on charge differences, thereby producing an antimicrobial peptide.

2. The method according to claim 1, wherein the termination codon of the first cistron is UAA or UGA and wherein the termination codon of the first cistron overlaps with an initiation codon of the second cistron such that the first and second cistrons of the DNA construct are connected by a UAAUG or UGAUG nucleotide sequence.

3. The method according to claim 1, wherein the basic antimicrobial peptide is any one of histonin II, parasin, and pexiganan.

4. The method according to claim 1, wherein the acidic peptide has one or more disulfide bonds.

5. The method according to claim 1, wherein the acidic peptide is any one of the peptides selected from the group consisting of mIF1 having the amino acid sequence as set forth in SEQ ID NO: 1, mIF2 having the amino acid sequence as set forth in SEQ ID NO: 2, and mIF3 having the amino acid sequence as set forth in SEQ ID NO:3.

* * * * *

SEQUENCE LISTING

```
<160> NUMBER OF SEQ ID NOS: 20

<210> SEQ ID NO 1
<211> LENGTH: 150
<212> TYPE: PRT
<213> ORGANISM: Artificial Sequence
<220> FEATURE:
<223> OTHER INFORMATION: mIF1 peptide

<400> SEQUENCE: 1

Cys Tyr Cys Gln Asp Pro Tyr Val Lys Glu Ala Glu Asn Leu Lys Lys
1               5                   10                  15

Tyr Phe Asn Ala Gly His Ser Asp Val Ala Asp Asn Gly Thr Leu Phe
            20                  25                  30

Leu Gly Ile Leu Lys Asn Trp Lys Glu Glu Ser Asp Arg Lys Ile Met
        35                  40                  45

Gln Ser Gln Ile Val Ser Phe Tyr Phe Lys Leu Phe Lys Asn Phe Lys
    50                  55                  60

Asp Asp Gln Ser Ile Gln Lys Ser Val Glu Thr Ile Lys Glu Asp Met
65                  70                  75                  80

Asn Val Lys Phe Phe Asn Ser Asn Lys Lys Arg Asp Asp Phe Glu
                85                  90                  95

Lys Leu Thr Asn Tyr Ser Val Thr Asp Leu Asn Val Gln Arg Lys Ala
            100                 105                 110

Ile His Glu Leu Ile Gln Val Met Ala Glu Leu Ser Pro Ala Ala Lys
        115                 120                 125

Thr Gly Lys Arg Lys Arg Ser Gln Met Leu Phe Arg Gly Arg Arg Ala
    130                 135                 140

Ser Gln Glu Glu Val Glu
145                 150

<210> SEQ ID NO 2
<211> LENGTH: 92
<212> TYPE: PRT
<213> ORGANISM: Artificial Sequence
<220> FEATURE:
<223> OTHER INFORMATION: mIF2 peptide

<400> SEQUENCE: 2

Cys Tyr Cys Gln Asp Pro Tyr Val Lys Glu Ala Glu Asn Leu Lys Lys
1               5                   10                  15

Tyr Phe Asn Ala Gly His Ser Asp Val Ala Asp Asn Gly Thr Leu Phe
            20                  25                  30

Leu Gly Ile Leu Lys Asn Trp Lys Glu Glu Ser Asp Arg Lys Ile Met
        35                  40                  45

Gln Ser Gln Ile Val Ser Phe Tyr Phe Lys Leu Phe Lys Asn Phe Lys
    50                  55                  60

Asp Asp Gln Ser Ile Gln Lys Ser Val Glu Thr Ile Lys Glu Asp Met
65                  70                  75                  80

Asn Val Lys Phe Phe Asn Ser Asn Glu Glu Val Glu
                85                  90

<210> SEQ ID NO 3
<211> LENGTH: 63
```

```
<212> TYPE: PRT
<213> ORGANISM: Artificial Sequence
<220> FEATURE:
<223> OTHER INFORMATION: mIF3 peptide

<400> SEQUENCE: 3

Cys Tyr Cys Gln Asp Pro Tyr Val Lys Glu Ala Glu Asn Leu Lys Lys
 1               5                  10                  15

Tyr Phe Asn Ala Gly His Ser Asp Val Ala Asp Asn Gly Thr Leu Phe
             20                  25                  30

Leu Gly Ile Leu Lys Asn Trp Lys Glu Glu Ser Asp Arg Lys Ile Met
         35                  40                  45

Gln Ser Gln Ile Val Ser Phe Tyr Phe Lys Leu Glu Glu Val Glu
     50                  55                  60

<210> SEQ ID NO 4
<211> LENGTH: 12
<212> TYPE: DNA
<213> ORGANISM: Artificial Sequence
<220> FEATURE:
<223> OTHER INFORMATION: Shine-Dalgarno cistron
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (9)..(12)
<223> OTHER INFORMATION: n is a, c, g, or t

<400> SEQUENCE: 4
naggaggtnn nn                                                              12

<210> SEQ ID NO 5
<211> LENGTH: 12
<212> TYPE: DNA
<213> ORGANISM: Artificial Sequence
<220> FEATURE:
<223> OTHER INFORMATION: example Shine-Delgarno cistron

<400> SEQUENCE: 5
gaggaggtgg aa                                                              12

<210> SEQ ID NO 6
<211> LENGTH: 21
<212> TYPE: PRT
<213> ORGANISM: Artificial Sequence
<220> FEATURE:
<223> OTHER INFORMATION: histonin II peptide

<400> SEQUENCE: 6

Arg Ala Gly Leu Gln Phe Pro Val Gly Arg Leu Leu Arg Arg Leu Leu
 1               5                  10                  15

Arg Arg Leu Leu Arg
             20

<210> SEQ ID NO 7
<211> LENGTH: 80
<212> TYPE: DNA
<213> ORGANISM: Artificial Sequence
<220> FEATURE:
<223> OTHER INFORMATION: mIF1 primer no. 1

<400> SEQUENCE: 7
tgttactgcc aggacccata tgtaaaagaa gcagaaaacc ttaagaaata ttttaatgca         60
ggtcattcag atctagcgga                                                    80
```

-continued

<210> SEQ ID NO 8
<211> LENGTH: 80
<212> TYPE: DNA
<213> ORGANISM: Artificial Sequence
<220> FEATURE:
<223> OTHER INFORMATION: mIF1 primer no. 2

<400> SEQUENCE: 8
atgtcctcgt cactctcctc tttccaattc ttcaaaatgc ctaagaaaag agttccatta    60
tccgctacat ctgaatgacc                                               80

<210> SEQ ID NO 9
<211> LENGTH: 80
<212> TYPE: DNA
<213> ORGANISM: Artificial Sequence
<220> FEATURE:
<223> OTHER INFORMATION: mIF1 primer no. 3

<400> SEQUENCE: 9
gaggagagtg acgaggacat aatgcagagc caaattgtct cctttactt caaactttt     60 aaaaactta aagatgacca                                                80

<210> SEQ ID NO 10
<211> LENGTH: 80
<212> TYPE: DNA
<213> ORGANISM: Artificial Sequence
<220> FEATURE:
<223> OTHER INFORMATION: mIF1 primer no. 4

<400> SEQUENCE: 10
ctattgaaaa acttgacatt catgtcttcc ttgatggtct ccacactctt ttggatgctc    60
tggtcatctt taaagttttt                                               80

<210> SEQ ID NO 11
<211> LENGTH: 80
<212> TYPE: DNA
<213> ORGANISM: Artificial Sequence
<220> FEATURE:
<223> OTHER INFORMATION: mIF1 primer no. 5

<400> SEQUENCE: 11
aatgtcaagt ttttcaatag caacaaaaag aaacgagatg acttcgaaaa gctgactaat    60
tattcggtaa ctgacttgaa                                               80

<210> SEQ ID NO 12
<211> LENGTH: 80
<212> TYPE: DNA
<213> ORGANISM: Artificial Sequence
<220> FEATURE:
<223> OTHER INFORMATION: mIF1 primer no. 6

<400> SEQUENCE: 12
gctgctggcg acagttcagc catcacttgg atgagttcat gtattgcttt gcgttggaca    60
ttcaagtcag ttaccgaata                                               80

<210> SEQ ID NO 13
<211> LENGTH: 78
<212> TYPE: DNA
<213> ORGANISM: Artificial Sequence
<220> FEATURE:
<223> OTHER INFORMATION: mIF1 primer no. 7

<400> SEQUENCE: 13

```
gctgaactgt cgccagcagc taaaacaggg gaagacgagg atagtcagat gctgtttcga    60
ggtcgaagag catcccag                                                  78

<210> SEQ ID NO 14
<211> LENGTH: 31
<212> TYPE: DNA
<213> ORGANISM: Artificial Sequence
<220> FEATURE:
<223> OTHER INFORMATION: mIF1 primer no. 8

<400> SEQUENCE: 14
ggaattccat atgtgttact gccaggaccc a                                   31

<210> SEQ ID NO 15
<211> LENGTH: 37
<212> TYPE: DNA
<213> ORGANISM: Artificial Sequence
<220> FEATURE:
<223> OTHER INFORMATION: mIF1 primer no. 9

<400> SEQUENCE: 15
cattattcca cctcctcctg ggatgctctt cgacctc                             37

<210> SEQ ID NO 16
<211> LENGTH: 38
<212> TYPE: DNA
<213> ORGANISM: Artificial Sequence
<220> FEATURE:
<223> OTHER INFORMATION: mIF2 primer no. 10

<400> SEQUENCE: 16
cattattcca cctcctcgtt gctattgaaa aacttgac                            38

<210> SEQ ID NO 17
<211> LENGTH: 38
<212> TYPE: DNA
<213> ORGANISM: Artificial Sequence
<220> FEATURE:
<223> OTHER INFORMATION: mIF3 primer no. 11

<400> SEQUENCE: 17
cattattcca cctcctcaag tttgaagtaa aaggagac                            38

<210> SEQ ID NO 18
<211> LENGTH: 57
<212> TYPE: DNA
<213> ORGANISM: Artificial Sequence
<220> FEATURE:
<223> OTHER INFORMATION: histonin II primer no. 12

<400> SEQUENCE: 18
gaggaggtgg aataatgcgt gctggtctgc agttcccggt tggtcgtctg ctgcgtc       57

<210> SEQ ID NO 19
<211> LENGTH: 50
<212> TYPE: DNA
<213> ORGANISM: Artificial Sequence
<220> FEATURE:
<223> OTHER INFORMATION: histonin II primer no. 13

<400> SEQUENCE: 19
cgggatcctc aacgcagcag acgacgcagc agacgacgca gcagacgacc               50

<210> SEQ ID NO 20
<211> LENGTH: 4
```

```
<212> TYPE: PRT
<213> ORGANISM: Artificial Sequence
<220> FEATURE:
<223> OTHER INFORMATION: SEQ ID NO: 5 peptide

<400> SEQUENCE: 20

Glu Glu Val Glu
1
```